US012466210B2

(12) United States Patent
Kubo et al.

(10) Patent No.: US 12,466,210 B2
(45) Date of Patent: Nov. 11, 2025

(54) SHAFT BODY OF PENCIL OR COSMETIC

(71) Applicant: MITSUBISHI PENCIL COMPANY, LIMITED, Tokyo (JP)

(72) Inventors: Ryota Kubo, Fujioka (JP); Satoru Banzai, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 0 days.

(21) Appl. No.: 18/699,664

(22) PCT Filed: Oct. 7, 2022

(86) PCT No.: PCT/JP2022/037648

§ 371 (c)(1),
(2) Date: Apr. 9, 2024

(87) PCT Pub. No.: WO2023/063259

PCT Pub. Date: Apr. 20, 2023

(65) Prior Publication Data

US 2024/0424825 A1 Dec. 26, 2024

(30) Foreign Application Priority Data

Oct. 15, 2021 (JP) ................................ 2021-169429

(51) Int. Cl.

| | |
|---|---|
| ***B43K 19/02*** | (2006.01) |
| ***A45D 40/20*** | (2006.01) |
| ***A61K 8/02*** | (2006.01) |
| ***A61Q 1/02*** | (2006.01) |
| ***B43K 19/14*** | (2006.01) |
| ***B43K 19/16*** | (2006.01) |

(52) U.S. Cl.

CPC .............. *B43K 19/02* (2013.01); *A45D 40/20* (2013.01); *A61K 8/0229* (2013.01); *A61Q 1/02* (2013.01); *B43K 19/14* (2013.01); *B43K 19/145* (2013.01); *B43K 19/16* (2013.01)

(58) Field of Classification Search

CPC ........ B43K 19/02; B43K 19/00; B43K 19/14; B43K 19/145; B43K 19/16; A45D 40/20; A61K 8/0229; A61K 8/027; A61Q 1/02

USPC ........................................ 401/49, 50, 88, 96

See application file for complete search history.

(56) References Cited

U.S. PATENT DOCUMENTS

| | | | | |
|---|---|---|---|---|
| 5,346,930 | A | 9/1994 | Maine et al. | |
| 5,371,037 | A * | 12/1994 | Yonehara | H01L 21/76243 117/10 |
| 6,168,857 | B1 * | 1/2001 | Andersen | B29C 71/0009 428/297.4 |
| 6,478,494 | B1 | 11/2002 | Eckl et al. | |
| 2010/0003061 | A1 | 1/2010 | Andreas | |
| 2021/0024706 | A1 | 1/2021 | Mayes et al. | |

FOREIGN PATENT DOCUMENTS

| | | | |
|---|---|---|---|
| JP | 60-204399 | A | 10/1985 |
| JP | 5-96899 | A | 4/1993 |
| JP | 6-255296 | A | 9/1994 |
| JP | 2001-192502 | A | 7/2001 |
| JP | 2002-529273 | A | 9/2002 |
| JP | 2014-019042 | A | 2/2014 |
| JP | 2021-520307 | A | 8/2021 |

OTHER PUBLICATIONS

International Search Report mailed on Nov. 22, 2022 in PCT/JP2022/037648 filed on Oct. 7, 2022.

* cited by examiner

*Primary Examiner* — David J Walczak

(74) *Attorney, Agent, or Firm* — Oblon, McClelland, Maier & Neustadt, L.L.P.

(57) ABSTRACT

A shaft body for a pencil lead (including a color pencil lead) or a shaft body for a cosmetic such as a rod-shaped cosmetic including an eye liner, an eyebrow pencil, or an eye shadow, which has the same ease of shaving as a conventional wood shaft and has a low impact on the environment. The shaft body for a pencil or a cosmetic according to the present disclosure is a shaft body for a pencil or a cosmetic constituted by coating a pencil lead or a rod-shaped cosmetic with a shaft body material composition, and the shaft body material composition contains at least a naturally-derived constitutional material and a naturally-derived binder.

11 Claims, No Drawings

SHAFT BODY OF PENCIL OR COSMETIC

TECHNICAL FIELD

The present specification relates to a shaft body for a pencil lead or a cosmetic that has a low impact on the environment, and can be easily produced, while it has the same ease of shaving, drop resistance, and water resistance as a conventional wood shaft.

BACKGROUND ART

For a shaft body of a pencil, a rod-shaped cosmetic, or the like, natural wood materials that provide a pleasing tactile experience to the user, in particular, red cedar produced in the United States, is used because those are soft and easy to shave with a knife or a pencil sharpener.

Meanwhile, in recent years, natural wood materials have been decreasing due to over-cutting such as deforestation, and under such circumstances, attention has been paid to the issue of environmental destruction. Red cedar and the like also have become difficult to obtain, and alternative materials have been developed.

Typically, as a technology for alternative materials for a shaft body of a pencil, a rod-shaped cosmetic, or the like, for example, the following is known:

1) a pencil constituted by continuously and integrally forming projections and recesses alternately on a rod-shaped outer peripheral surface of a lead material containing a thermoplastic resin, a lubricant, and graphite or a pigment, forming a shaft material containing a thermoplastic resin, a cellulose fiber, and a foaming agent on the outside of the lead material to be in close contact with the uneven surface of the lead material, and introducing a part of the cellulose fiber in the shaft material into uneven portions of the rod-shaped outer peripheral surface of the lead material in a biting manner (for example, see Patent Document 1);
2) for providing a pencil that has no issues even when the pencil is sharpened with a pencil sharpener, and can be produced inexpensively because of its shaft being excellent in processability, a pencil constituted by mixing cellulose fine powder particles subjected to grinding treatment into a resin, molding the mixture by extruding or injection molding, further forming the molded body into a shaft shape for a pencil to obtain a shaft, and inserting a lead into the shaft (for example, see Patent Document 2);
3) for providing a biodegradable synthetic shaft for a pencil-type cosmetic product that has excellent physical properties such as rigidity, shaving property, and oil and fat penetration resistance, and a good feeling of use as a synthetic shaft replacing a wood shaft, is easily decomposed after disposal, can be burned with a low calorific value, and does not generate a harmful substance at the time of incineration, and a production method therefor, a hollow cylindrical biodegradable synthetic shaft for a pencil-type cosmetic product constituted by molding using a biodegradable thermoplastic material including a starch ester in which hydrogen atoms of reactive hydroxyl groups of identical starch molecules are substituted with a short-chain acyl group and a long-chain acyl group and a reinforcing filler as a base material (see, for example, Patent Document 3); and
4) a pencil in which a surface of a shaft made of wood is coated with a foamed resin coating layer formed with a thermally foamable resin (see, for example, Patent Document 4).

However, in the above Patent Documents 1 to 4, there is still a high impact on the environment, and when an attempt is made to produce a product with a low impact on the environment, there are issues in that the ease of shaving, drop resistance, water resistance, and the like are reduced.

CITATION LIST

Patent Document

Patent Document 1: JP S60-204399 A (Claims, Examples, etc.)

Patent Document 2: JP H06-255296 A (Claims, Examples, etc.)

Patent Document 3: JP 2001-192502 A (Claims, Examples, etc.)

Patent Document 4: JP 2014-019042 A (Claims, Examples, etc.)

SUMMARY OF INVENTION

Technical Problem

The present disclosure has been made to solve the above-described known issues and the like, and an object of the present disclosure is to provide a shaft body for a pencil lead or a rod-shaped cosmetic, which has the same ease of shaving, drop resistance, and water resistance as a conventional wood shaft, has a low impact on the environment, and can be easily produced.

Solution to Problem

As a result of intensive study on the above-described known issues, the present disclosers have found that the shaft body for a pencil or a cosmetic for the above object can be obtained from a shaft body for a pencil or a cosmetic constituted by coating a pencil lead or a rod-shaped cosmetic with a shaft body material composition, in which the shaft body material composition contains at least a specific constitutional material and a binder, and have completed the present disclosure.

That is, the shaft body for a pencil or a cosmetic of the present disclosure is characterized by a shaft body for a pencil or a cosmetic constituted by coating a pencil lead or a rod-shaped cosmetic with a shaft body material composition, in which the shaft body material composition contains at least a naturally-derived constitutional material and a naturally-derived binder.

The shaft body material composition preferably has a natural origin index (not including water) of 75% or more.

Furthermore, in the shaft body material composition, it is preferable that the naturally-derived binder is carboxymethyl cellulose or a salt thereof, or a crosslinking agent having a carboxylic acid group ester-crosslinking the binder is contained.

A pencil according to the present disclosure is a pencil including at least a pencil lead and a shaft body constituted by coating and molding the pencil lead, in which the shaft body is a shaft body having the above-described configuration. A rod-shaped cosmetic product according to the present disclosure is a rod-shaped cosmetic product including at least a rod-shaped cosmetic and a shaft body constituted by coating and molding the rod-shaped cosmetic, in which the shaft body is a shaft body having the above-described configuration.

Advantageous Effects of Invention

According to the present disclosure, provided is a shaft body for a pencil lead or a cosmetic that has the same ease of shaving and drop resistance as a conventional wood shaft, has a low impact on the environment, and can be easily produced, as well as a pencil, a rod-shaped cosmetic product, or the like including the foregoing shaft body.

The object and effects of the present disclosure can be recognized and obtained especially using the components and combinations indicated in the claims. Both general explanation described above and detailed explanation described below are exemplary and explanatory and do not limit the present disclosure described in Claims.

DESCRIPTION OF EMBODIMENTS

Hereinafter, embodiments of the present disclosure will be described in detail. Note that the technical scope of the present disclosure is not limited to the embodiment described below but includes the invention described in Claims and equivalents thereof. In addition, the present disclosure can be implemented based on the contents disclosed in the present specification and technical common knowledge (including design matters and obvious matters) in the art.

The shaft body for a pencil or a cosmetic of the present disclosure is a shaft body for a pencil or a cosmetic constituted by coating a pencil lead or a rod-shaped cosmetic with a shaft body material composition, in which the shaft body material composition contains at least a naturally-derived constitutional material and a naturally-derived binder.

Examples of the naturally-derived constitutional material to be used in the present disclosure include sawdust, wood powder, powdery cellulose, obtained from naturally-derived wood materials, and naturally-derived inorganic powder.

The sawdust to be used is not particularly limited but can be derived from hardwood or softwood. Specific examples of tree species of the sawdust to be used in the present disclosure include cedar, pine, larch, red pine, Sakhalin Fir, cypress, beech, horse chestnut, Quercus serrata, Quercus crispula, oak, Japanese linden, birch, Japanese Elm, lauan, and Western hemlock. In particular, cedar, cypress sapwood, beech, horse chestnut, Quercus crispula, or the like is preferably used. In addition, waste materials generated during production of these wood materials may be effectively utilized. Further, at least one kind (one kind or a combination of two or more kinds; the same applies hereinafter) of these kinds of sawdust can be used.

Regarding the size of the sawdust, from the viewpoint of dispersibility, moldability, and the like, it is desirable that the average particle size is 10 mesh or more, and it is further desirable to use sawdust in a range of 200 mesh or less from the viewpoint of an energy cost required for pulverization.

As the wood powder that can be used, for example, at least one kind of wood powder obtained from each tree species exemplified in the above-described sawdust, wood powder obtained from the above-described sawdust or waste wood, sander powder, or the like can be used. To further improve the dispersibility and moldability, the upper limit of the average particle size of the wood powder is preferably, for example, 2000 μm or less, and the lower limit thereof is preferably, for example, 100 μm or more. However, the wood powder may be in the form of a microfibrillated fiber. Note that the average particle size in the present disclosure can be a value measured in accordance with a laser diffraction/scattering method.

The powdery cellulose that can be used is preferably cellulose powder obtained by finely pulverizing naturally-derived cellulose fibers of a plant, and preferably, the average particle size thereof is 100 μm or less, preferably in a range of 10 to 50 μm. As the powdery cellulose, for example, crystalline cellulose powder having a certain particle size distribution produced by a method of purifying, drying, and pulverizing/sieving an undecomposed residue obtained after acid hydrolysis of selected pulp may be used, or a commercially available product such as the trade name "KC Flock" (available from Nippon Paper Chemicals Co., Ltd.), the trade name "Ceolus" (available from Asahi Kasei Chemicals Corporation), or the trade name "Avicel" (available from FMC Corporation) may be used.

The naturally-derived inorganic powder that can be used include at least one of: talc, calcium carbonate, huntite, kaolin, sericite, bentonite, titanium oxide, or the like.

The upper limit of the average particle size of these kinds of inorganic powder is preferably, for example, 50 μm or less, and the lower limit thereof is preferably, for example, 1 μm.

The content of these naturally-derived constitutional materials is preferably 60 to 90 mass %, and more preferably 70 to 80 mass %, relative to the total amount of the shaft body material composition. When the content of the naturally-derived constitutional material is 60 mass % or more, usable shaving property can be achieved, and when the content is 90 mass % or less, usable strength can be achieved.

In addition, when the proportion of the inorganic powder in the naturally-derived constitutional material is 60 mass % or less, drop resistance of the shaft body is improved, and it is possible to prevent breakage the pencil lead or the rod-shaped cosmetic inside in a case where the shaft body is used for a pencil or a cosmetic.

As the naturally-derived binder to be used in the present disclosure, at least one of cellulose fibers (including nanofibers), methylcellulose or a salt thereof, carboxymethylcellulose or a salt thereof, hydroxymethylpropylcellulose or a salt thereof, cellulose acetate or a salt thereof, sodium alginate, or the like can be used. Examples of the salt of each kind of cellulose described above include sodium, ammonium, and calcium.

These binders are preferably water-soluble, and further, the naturally-derived binder is preferably carboxymethyl cellulose ammonium from the viewpoint of imparting water resistance.

The content of the naturally-derived binders is preferably 10 to 40 mass %, and more preferably 20 to 30 mass %, relative to the total amount of the shaft body material composition.

When the content of the naturally-derived binder is 10 mass % or more, usable strength can be achieved, and when the content is 40 mass % or less, usable shaving property can be achieved.

The shaft body material composition according to the present disclosure may further contain, in addition to the naturally-derived constitutional material and the naturally-derived binder, a crosslinking agent for crosslinking the binder, from the viewpoint of further exhibiting the effects of the present disclosure and imparting water resistance.

The crosslinking agent for crosslinking the binder is preferably a crosslinking agent having a carboxylic acid group that ester-crosslinks the binder, and specific examples thereof include succinic acid, malic acid, maleic acid, tartaric acid, citric acid, and polyacrylic acid.

The content of the crosslinking agent is preferably 0.1 to 5 mass %, and more preferably 0.5 to 2 mass % relative to the total amount of the shaft body material composition, from the viewpoint of exhibiting water resistance, suppressing a decrease in strength due to moisture absorption, and suppressing discoloration of the material.

Furthermore, the shaft body material composition of the present disclosure may appropriately contain a coloring agent (dye, inorganic pigment, organic pigment) for coloring the shaft body, iron oxide, zinc oxide, carbon black, natural pigment, or the like as necessary, in addition to the naturally-derived constitutional material, the naturally-derived binder, and the crosslinking agent described above.

These shaft body material compositions preferably have a natural origin index (not including water) of 75% or more from the viewpoint of further exhibiting the effects of the present disclosure and from the viewpoint of impact on the environment.

The term "natural origin index (not including water)" refers to an index expression according to ISO 16128, and when the natural origin index (not including water) is 75% or more, more preferably 85% or more, a shaft body for a pencil lead or a cosmetic, which has an extremely low impact on the environment, can be obtained.

The natural origin index (not including water) of the shaft body material composition can be set to 75% or more by appropriately selecting the naturally-derived constitutional material and the naturally-derived binder described above.

The shaft body for a pencil or a cosmetic of the present disclosure is obtained as follows. A blended composition including the naturally-derived constitutional material, the naturally-derived binder, and the like described above is dry-mixed using a kneading apparatus such as a Henschel mixer, a planetary mixer, a kneader, or the like, and then, water (purified water, distilled water, or the like) is added to the mixture to achieve a moisture content of 40 to 80%, thereby obtaining a slurry. The slurry is further kneaded while warming, degassing, or the like is performed to obtain a clay-like mixture having a moisture content of about 30 to 60%. An extrusion-molding machine or the like is used to get the mixture on an outer periphery of a pencil lead or a cosmetic to be coated using a die having a predetermined diameter, and the resulting product is dried, whereby a pencil or a cosmetic is obtained. Alternatively, a pencil or a cosmetic can also be obtained by a method in which the kneaded product is molded into a round bar or a plate shape using an extrusion-molding machine or the like with a die having a predetermined diameter or a T-die and then dried to produce a molded body, to which a pencil lead or a cosmetic is inserted after processed. Note that the physical properties of the shaft body can be controlled in a wide range by a pressing pressure in extrusion molding or the like, a moisture content, and combination of the naturally-derived constitutional material, the naturally-derived binder, and the like, and thus, a shaft body suitable for a pencil or a cosmetic, which can satisfy required texture, strength, moldability, and the like of the shaft body, can be obtained.

In the present disclosure, a composition, a form, and the like of the pencil lead to be coated with the shaft body material composition are not particularly limited, and examples of the pencil lead include a fired pencil lead (including a fired color pencil lead) and a non-fired pencil lead (including a non-fired color pencil lead). Examples of the fired pencil lead include a fired pencil lead obtained by mixing, dispersing, and kneading materials including a coloring component such as graphite, an organic binder such as a vinyl chloride resin, a vinylidene chloride resin, a vinyl acetate resin, chlorinated polyethylene, polyvinyl alcohol, an acryl amide resin, a chlorinated paraffin resin, a phenol resin, a furan resin, an urea resin, or butyl rubber, a plasticizer such as a phthalic acid ester, a solvent such as methyl ethyl ketone or water, a stabilizer such as a stearate, a lubricant such as stearic acid, and a filling material such as carbon black, extrusion-molding the kneaded mixture into a thin line shape, heat-treating the molded product to a firing temperature to obtain a lead body, and impregnating the obtained lead body with an oily substance such as a silicone oil, liquid paraffin, spindle oil, squalane, or an α-olefin oligomer, or a wax.

A composition, a form, and the like of the rod-shaped cosmetic to be coated with the shaft body material composition are not particularly limited, and examples thereof include a cosmetic obtained by kneading blending components to be used for an eye liner, an eyebrow pencil, a lip liner, a concealer pencil, an eye shadow, or the like, for example, a wax such as oil and fat, wax, fatty acid, or hydrocarbon, or a clay as a binder, a colorant, and a constitutional material, and molding the mixture into a rod shape. The rod-shaped cosmetic may be a fired rod-shaped cosmetic stick or a non-fired rod-shaped cosmetic.

The shaft body for a pencil lead or a cosmetic of the present disclosure configured as described above has the same ease of shaving, drop resistance, and water resistance as a conventional wood shaft, and has a low impact on the environment. A conventional molding machine or the like used for molding a pencil or a cosmetic can be used without modification, and thus, it is possible to easily produce the shaft body for a pencil lead or a cosmetic.

The pencil according to the present disclosure is characterized in that at least, the shaft body constituted by coating and molding the above-described pencil lead is the shaft body having the above-described configuration, and the rod-shaped cosmetic product according to the present disclosure is characterized in that at least, the shaft body constituted by coating and molding the above-described rod-shaped cosmetic is the shaft body having the above-described configuration.

In the present disclosure, the pencil lead or the rod-shaped cosmetic can be molded into any shape, for example, a shape having a cross-sectional shape such as a circular shape (including an elliptical shape) or a polygonal shape such as a triangular shape or a hexagonal shape, or a tubular shape, and thus can be formed into a pencil or a rod-shaped cosmetic product having each shape by various processing methods such as coating molding and shaving processing.

EXAMPLES

Herein after, the present disclosure will be described using Examples and Comparative Examples, but the present disclosure is not limited to these Examples.

For the pencil leads of Examples 1 to 8 and Comparative Example 1, pencil leads obtained by the following production method were used.

After 60 mass % of graphite and 40 mass % of clay were dry-mixed by a Henschel mixer, purified water was added thereto to achieve a moisture content of 40%, followed by kneading. The obtained slurry was kneaded while being warmed and degassed to obtain a clay-like mixture having a moisture content of about 30%. This mixture was molded using a hydraulic plunger-type extrusion-molding machine with a die having a diameter of 2.5 mm, and the molded body was dried under an environment of 60° C., and then calcined at 800 to 1400° C. for 12 to 24 hours to obtain a lead body having a diameter of 2.0 mm. The obtained lead body was impregnated with an α-olefin oligomer to obtain a pencil lead having a diameter of 2.0 mm and a hardness of HB.

Example 1

Huntite powder (average particle size 2 μm) 90 mass %
Cellulose powder (average particle size 45 μm) 10 mass %

The natural origin index (not including water) of this shaft body material composition was 100.0%.

After the blended composition was dry-mixed by a Henschel mixer, purified water was added thereto to achieve a moisture content of 40%, followed by kneading.

The obtained slurry was kneaded while being warmed and degassed to obtain a clayey mixture having a moisture content of about 30%. A hydraulic plunger-type extrusion-molding machine was used with a die having a diameter of 9.0 mm to coat an outer periphery of the pencil lead having a diameter of 2.0 mm and a hardness of HB with the materials.

The molded body was dried in an environment of 60° C. to obtain a pencil.

Example 2

Sawdust of cedar-based wood material (16 mesh) 70 mass % Sodium carboxymethylcellulose 30 mass %

The natural origin index (not including water) of this shaft body material composition was 92.5%.

After the blended composition was dry-mixed by a Henschel mixer, purified water was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C. to obtain a pencil.

Example 3

Talc (average particle size 8 μm) 40 mass %
Sawdust of cedar-based wood material (16 mesh) 40 mass %
Sodium carboxymethylcellulose 20 mass %

The natural origin index (not including water) of this shaft body material composition was 95.0%.

After the blended composition was dry-mixed by a Henschel mixer, purified water was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C. to obtain a pencil.

Example 4

Talc (average particle size 8 μm) 30 mass %
Cellulose powder (average particle size 45 μm) 60 mass %
Sodium carboxymethylcellulose 10 mass %

The natural origin index (not including water) of this shaft body material composition was 97.5%.

After the blended composition was dry-mixed by a Henschel mixer, purified water was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C. to obtain a pencil.

Example 5

Talc (average particle size 8 μm) 30 mass %
Cellulose powder (average particle size 45 μm) 60 mass %
Carboxymethylcellulose ammonium 10 mass %

The natural origin index (not including water) of this shaft body material composition was 97.5%.

After the blended composition was dry-mixed by a Henschel mixer, purified water was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C. and heated at 180° C. to make the binder water-insoluble, thereby obtaining a pencil.

Example 6

Talc (average particle size 8 μm) 30 mass %
Cellulose powder (average particle size 45 μm) 60 mass %
Sodium carboxymethylcellulose 10 mass %

The natural origin index (not including water) of this shaft body material composition was 97.5%.

After the blended composition was dry-mixed by a Henschel mixer, a 5% aqueous succinic acid solution was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C., and then heated at 180° C. to crosslink the binder, thereby obtaining a pencil.

Example 7

Talc (average particle size 8 μm) 30 mass %
Cellulose powder (average particle size 45 μm) 60 mass %
Methylcellulose 10 mass %

The natural origin index (not including water) of this shaft body material composition was 97.5%.

After the blended composition was dry-mixed by a Henschel mixer, purified water was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C. to obtain a pencil.

Example 8

Talc (average particle size 8 μm) 30 mass %

Cellulose powder (average particle size 45 μm) 60 mass %

Methylcellulose 10 mass %

The natural origin index (not including water) of this shaft body material composition was 97.5%.

After the blended composition was dry-mixed by a Henschel mixer, a 5% aqueous succinic acid solution was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat an outer periphery of the pencil lead having a diameter of 2.0 mm and a hardness of HB with the materials. The molded body was dried in an environment of 60° C., and then heated at 180° C. to crosslink the binder, thereby obtaining a pencil.

Example 9

<Preparation of Solid Cosmetic>

Beeswax 20 parts

Ozokerite 10 parts

Microcrystalline wax 10 parts

Vaseline 7 parts

Carnauba wax 8 parts

Lanolin 5 parts

Liquid paraffin 7 parts

Isopropyl myristate 4 parts

The above blending materials were dissolved, 10 parts of black iron oxide and 19 parts of red iron oxide were added thereto (total amount: 100 parts), and the mixture was stirred and dispersed, followed by kneading by a mixer. The kneaded mixture was cooled to room temperature and molded by an extrusion-molding machine to obtain a brown solid cosmetic of 2.0 mm.

Talc (average particle size 8 μm) 30 mass %

Cellulose powder (average particle size 45 μm) 60 mass %

Methylcellulose 10 mass %

The natural origin index (not including water) of the shaft body material composition was 97.5%.

After the blended composition was dry-mixed by a Henschel mixer, purified water was added thereto to achieve a moisture content of 50%, followed by kneading. The obtained slurry was kneaded while being warmed and degassed to obtain a clay-like mixture having a moisture content of about 40%. A hydraulic plunger-type extrusion-molding machine was used with a die having a diameter of 9.0 mm to coat the solid cosmetic having a diameter of 2.0 mm with the mixture. The molded body was dried in an environment of 60° C. to obtain a rod-shaped cosmetic product.

Comparative Example 1

Pencil (a pencil constituted by covering a pencil lead having a diameter of 2.0 mm and a hardness of HB with a cutting-processed incense cedar plate material impregnated with 2 wt % of paraffin wax)

Comparative Example 2

This is a pencil in which a conventional recycled natural material is used and a thermoplastic resin is used as a binder, and thus a non-naturally-derived material is used. The shaft body has the following composition and has a natural origin index of 70.0%.

Polypropylene (PP) 20 mass %

Wood powder 70 mass %

Maleic anhydride-grafted polypropylene 1 mass %

Amide wax 3 mass %

Stearic acid 1 mass %

Boron nitride 5 mass %

The pencils of Examples 1 to 9 and Comparative Examples 1 and 2 obtained as described above were evaluated for the natural origin index and ease of shaving by the following evaluation method.

These results are indicated in Table 1 below.

(Natural Origin Index)

The natural origin index (not including water) of each of the shaft bodies of Examples 1 to 9 and Comparative Examples 1 and 2 is obtained by calculating a composition ratio in percentage using a weight not including water of a natural raw material and a naturally-derived portion in a naturally-derived raw material defined in ISO 16128 from weight ratios of raw materials blended in the shaft material not including a lead. The higher this value is, the higher the ratio of an animal- or plant-derived material is, and the smaller an amount of a petroleum-derived material used is, which can indicate that the environmental impact is low.

(Evaluation Method for Ease of Shaving)

For each of the pencils of Examples 1 to 9 and Comparative Examples 1 and 2, after the tip was trimmed to have a diameter of 2 mm using a pencil sharpener, the pencil was shaved with a pencil sharpener mounted on a fixture connected to a rotation moment measuring apparatus until the lead became sharp by rotating the opposite side to the pencil sharpener with a hand. A peak value of a rotation moment during this performance was measured and evaluated the ease of shaving (shaving property) according to the following evaluation criteria. It can be said that when this value is less than 0.1 N, the pencil is easy to shave, and when the value exceeds 0.2 N·m, the pencil is hard and difficult to shave.

Evaluation Criteria:

A: can be easily shaved (less than 0.1 N·m)

B: can be shaved (0.1 N·m or more and less than 0.2 N·m)

C: hard to be shaved (0.2 N·m or more)

TABLE 1

| | Non-naturally-derived material | Natural origin index | Ease of shaving |
|---|---|---|---|
| Example 1 | Absent | 100.0% | A |
| Example 2 | Absent | 92.5% | B |

TABLE 1-continued

| | Non-naturally-derived material | Natural origin index | Ease of shaving |
|---|---|---|---|
| Example 3 | Absent | 95.0% | B |
| Example 4 | Absent | 97.5% | A |
| Example 5 | Absent | 97.5% | A |
| Example 6 | Absent | 97.5% | A |
| Example 7 | Absent | 97.5% | A |
| Example 8 | Absent | 97.5% | A |
| Example 9 | Absent | 97.5% | A |
| Comparative Example 1 | Absent | 97.9% | A |
| Comparative Example 2 | Present | 70.0% | B |

In consideration of the evaluation results in Table 1 above, it has been confirmed that Examples 1 to 9 within the scope of the present disclosure have a low impact on the environment and can be easily produced while having the same ease of shaving as Comparative Examples 1 and 2. In addition, in Examples 2 to 9, free falling was performed from a height of 75 cm to a concrete floor ten times for evaluation by setting the inorganic powder ratio in the constitutional material to 60% or less while maintaining a high natural origin index. As a result, it has been confirmed that the pencils, cosmetic, or the rod-shaped cosmetic were not damaged and had sufficient drop resistance. Furthermore, for each of the pencils in which the naturally-derived binder is made water-insoluble by using carboxymethylcellulose or crosslinked by a crosslinking agent having a carboxylic acid group that performs ester crosslinking in Examples 5, 6, and 8, water resistance (water resistance after immersion of the produced pencil in purified water for 24 hours) was evaluated. As a result, it has been confirmed that the pencil was not broken down and it was possible to exhibit sufficient water resistance.

INDUSTRIAL APPLICABILITY

It is possible to obtain a shaft body for a pencil or a cosmetic suitable for pencils (including colored pencils) and rod-shaped cosmetics such as an eye liner, an eyebrow pencil, and an eye shadow.

The invention claimed is:

1. A shaft body for a pencil or a cosmetic constituted by coating a pencil lead or a rod-shaped cosmetic with a shaft body, the shaft body comprising:

a shaft body material composition including at least a naturally-derived constitutional material, a naturally-derived binder, and a crosslinking agent for crosslinking the binder.

2. The shaft body for a pencil or a cosmetic according to claim 1, wherein the shaft body material composition has a natural origin index (not including water) of 75% or more.

3. The shaft body for a pencil or a cosmetic according to claim 1, wherein the naturally-derived binder is carboxymethyl cellulose or a salt thereof.

4. The shaft body for a pencil or a cosmetic according to claim 1, wherein the crosslinking agent has a carboxylic acid group ester-crosslinking the binder.

5. A pencil comprising at least a pencil lead and a shaft body constituted by coating and molding the pencil lead, wherein the shaft body is the shaft body described in claim 1.

6. A rod-shaped cosmetic product comprising at least a rod-shaped cosmetic and a shaft body constituted by coating and molding the rod-shaped cosmetic, wherein the shaft body is the shaft body according to claim 1.

7. A shaft body for a pencil or a cosmetic constituted by coating a pencil lead or a rod-shaped cosmetic with a shaft body, the shaft body comprising:

a shaft body material composition comprising at least a naturally-derived constitutional material, and a naturally-derived binder, wherein the binder is carboxymethyl cellulose or a salt thereof.

8. The shaft body for a pencil or a cosmetic according to claim 7, wherein the binder is carboxymethyl cellulose ammonium.

9. The shaft body for a pencil or a cosmetic according to claim 7, wherein the shaft body material composition has a natural origin index (not including water) of 75% or more.

10. A pencil comprising at least a pencil lead and a shaft body constituted by coating and molding the pencil lead, wherein the shaft body is the shaft body according to claim 7.

11. A rod-shaped cosmetic product comprising at least a rod-shaped cosmetic and a shaft body constituted by coating and molding the rod-shaped cosmetic, wherein the shaft body is the shaft body according to claim 7.

* * * * *